United States Patent [19]

Keyes

[11] 4,204,040

[45] * May 20, 1980

[54] COPOLYMERIZATION OF PROTEINS ON AN INORGANIC SUPPORT

[75] Inventor: Melvin H. Keyes, Sylvania, Ohio

[73] Assignee: Technicon Instruments Corporation, Tarrytown, N.Y.

[*] Notice: The portion of the term of this patent subsequent to Oct. 15, 1991, has been disclaimed.

[21] Appl. No.: 852,635

[22] Filed: Nov. 18, 1977

[51] Int. Cl.² .............................................. C07G 7/02
[52] U.S. Cl. ..................................... 435/176; 435/175
[58] Field of Search .................. 195/63, 68, DIG. 11; 260/112 R; 435/174, 176, 177, 180, 175

[56] References Cited

U.S. PATENT DOCUMENTS

| | | | |
|---|---|---|---|
| 3,126,324 | 3/1964 | Mitz | 195/63 |
| 3,223,593 | 12/1965 | Aldrich et al. | 195/63 |
| 3,519,538 | 7/1970 | Messing et al. | 195/63 |
| 3,841,971 | 10/1974 | Messing | 195/63 |
| 3,850,751 | 11/1974 | Messing | 195/63 |
| 3,873,426 | 3/1975 | Katchalski et al. | 195/63 |
| 3,930,951 | 1/1976 | Messing | 195/63 |
| 3,982,997 | 9/1976 | Eaton et al. | 195/63 X |
| 4,004,979 | 1/1977 | Arrameas et al. | 195/68 |
| 4,008,126 | 2/1977 | Keyes | 195/63 |

*Primary Examiner*—David M. Naff
*Attorney, Agent, or Firm*—S. P. Tedesco; Robert S. Salzman

[57] ABSTRACT

A method for producing an immobilized protein composite, particularly using enzyme and non-enzyme proteins, comprising selecting at least a first protein which is rich in cysteine and/or cystine amino acid residues, and a second protein which is poor in cysteine and/or cystine amino acid residues. These two proteins are deposited on an inorganic support and maintained at a pH and temperature for sufficient time to facilitate the copolymerization of the two proteins.

17 Claims, No Drawings

COPOLYMERIZATION OF PROTEINS ON AN INORGANIC SUPPORT

BACKGROUND OF THE INVENTION

1. Field of the Invention

This invention relates to the immobilization of catalytically active proteins and more particularly to the immobilization of enzymes on inorganic support materials. Enzymes usually have high molecular weights, can catalyze numerous specific chemical reactions, and many techniques have been developed to physically or chemically immobilize enzymes on various support materials. The techniques were developed because enzymes are generally water soluble and thus are difficult to remove from the reaction media for reuse. The techniques were developed to immobilize or fix the enzymes on substantially water insoluble supports without loss of catalytic activity so that the enzyme, on its support, which is called the enzyme-support composite, could be used repeatedly. However, many currently used immobilization methods are not readily accomplished or reproduced, and tend to be expensive to use in commercial operations. The method of the present invention produces a reproducible composite with relative ease at a very low cost.

2. Description of the Prior Art

It is known that enzymes can be fixed or immobilized on both organic and inorganic supports. Enzymes can be immobilized on particles of various metal oxides so that the enzyme is bound or deposited on the surface of the oxide and is supported thereon to catalyze a specific reaction as shown for example in U.S. Pat. No. 3,850,751. This type of immobilization, while satisfactory, has the disadvantage that the enzyme tends to desorb or release itself from the surface of the support over a period of time. The activity of the composite gradually diminishes over the long term, and the sample being treated is contaminated with active enzyme which continues to react with the sample after it has been removed from the reaction chamber for analysis. Accordingly, data for a given sample or batch may be obtained which may not be truly representative of the nature of the sample.

Many techniques have been attempted to lessen the rate at which enzymes will desorb from a support structure. In U.S. Pat. No. 3,873,426, an enzyme and an organic dye, typically a halotriazine dye, are absorbed onto alumina below pH 7. This codeposition is stated to increase the affinity of the enzyme for the support. However, in such a technique, the enzyme and the added species in this example, the dye, can eventually desorb into the test sample at some finite rate. Therefore, another possible contaminent may be introduced into the test sample which may give false results when the sample being tested is examined spectrophotometrically or electrochemically.

U.S. Pat. No. 3,982,997 discloses the use of mixed metal oxides to immobilize enzymes and to increase the amount of deposition of the enzyme and stability of the composite. While with this technique the enzyme does exhibit an increased initial activity, it does not bind the enzyme to the support with an affinity which is a desired strength of binding.

Techniques also have been utilized to covalently link an enzyme to the support to circumvent the desorption problems encountered in the techniques discussed above. These techniques of covalent bonding have generally used a coupling agent which bonds to the support with one reactive group and bonds to the enzyme with another reactive group. These groups have generally been reactive species such as diazos, silanes, and the like. For examples of these coupling agents, reference is made to U.S. Pat. Nos. 3,930,951, and 3,519,538.

In other techniques, the enzyme is used as the acidic member in forming a salt pair with an anion exchange resin, e.g. U.S. Pat. No. 3,126,324. Similarly, many techniques of gel entrapment are known wherein the enzyme is trapped in a hydrogel while maintaining its catalytic activity, e.g. U.S. Pat. No. 3,223,593.

Some techniques involve cross-linking the deposited enzymes to each other. These methods involve the use of reactive cross-linking reagents such as glutaraldehyde, but the reagents may adversely affect the activity of the enzyme. Such a cross-linking procedure is disclosed in U.S. Pat. No. 4,004,979. Also, methods of using sulfhydryl groups on the enzyme to cross-link the enzymes to each other are known, e.g. U.S. Pat. No. 4,008,126. This sulfhydryl cross-linking, as disclosed in the above patent, requires that all proteins which are being deposited have a relatively high proportion of cysteine or cystine amino acid residues in their structure.

Although the method is satisfactory for enzymes having the relatively high proportion of cysteine or cystine residues, the method is not applicable to proteins having relatively low proportions of the residues.

Many of the above immobilization techniques have been used in large scale commercial operations, but have not been completely satisfactory, due to the expense in production of the composite, the lack of long-term stability of the composite, certain difficulties involved e.g. in purifying the coupling agents from the composite after its production, and in the gradual desorption of these reagents into delicate samples, or into electrode systems used to monitor product levels in reactors.

SUMMARY OF THE INVENTION

An object of the present invention is to provide a process which eliminates the use of highly reactive intermediate reagents that are presently required for protein cross-linking.

Another object of the present invention is to provide a process which can deposit and polymerize proteins having low cysteine or cystine amino acid contents.

A further object of the invention is to provide an enzyme-protein-support composite which comprises including an enzyme with low cystine or cysteine amino acid content which maintains its catalytic activity over long-term uses, and which is easily removed from the reaction media.

These objects are achieved by the process of the present invention by the production of an enzyme-protein-support composite which incorporates a protein or enzyme which has a low cystine or cysteine amino acid content with one which has a high content of these amino acids. The two proteins or enzymes are deposited on the support and cross-linked to form a copolymer of the two proteins wherein the separate types of proteins are incorporated as the monomers.

DETAILED DESCRIPTION OF THE INVENTION

In the practice of the present invention, the selection of the two proteins is important. All enzymes do not have high cysteine or cystine amino acid residue contents. As used herein, and in accordance with the practice in the art, all enzymes are proteins, whereas each protein does not necessarily have enzyme activity. One effective method to form a stable protein or enzyme-support composite is to deposit the enzyme onto the support and to cross-link each enzyme molecule to another by the use of a cross-linking reagent. Many times the cross-linking reagents are difficult to purify from the resultant composite, or they adversely affect the enzyme which is being deposited. An additional problem arises if the enzyme desired to be deposited has relatively few reactive residues which are susceptible to the well-known cross-linking agents.

To provide for the solution of this problem, the method of the present invention uses the chemical properties of a moiety common to many enzymes. In the present method, an enzyme is first selected which is desired to be immobilized. This method is particularly applicable to enzymes which have a total of two times the number of the cystine amino acid residues, plus the cysteine amino acid residues, equaling less than about 14 per molecule. Herein, every cystine or cysteine residue is considered as a possible reactant in the rearrangement reaction when in the reduced form, described in detail hereinafter. Once the enzyme is selected, a protein or another enzyme which is relatively abundant in cysteine and cystine amino acid residues is selected. A protein abundant in the residues is defined as one having a total of two times the number of cystines and all of the cysteine of amino acid residue content greater than 14 per molecule. The two proteins are then deposited, under suitable conditions, on an inorganic support. The proteins are then subjected to conditions which bring about the cross-linking of the respective proteins on the surface of the support. It appears that the immobilization reaction involves a disulfide rearrangement within the protein molecule. Either the cystine or cysteine amino acid residues can total zero as long as the sum total of the two residues fulfills the 14 residue parameters set forth above. However, when no cysteine is present in one of the proteins, it may be necessary to add a small amount of a compound containing a sulfhydryl e.g. the reaction mixture contains $10^{-8}$ to $10^{-5}$ molar sulfhydryl groups, such as beta-mercaptoethanol, to initiate the disulfide rearrangement. The term "amino acid residue" is used herein in its conventional sense and refers to the residues of the amino acids which chemically combine to form the protein molecule.

It is known that the cysteine amino acid residues contain the —SH group and the cystine contains the —S—S— group, and under pH condition specified herein, these groups undergo a disulfide rearrangement which results in the polymerization of the protein. This disulfide rearrangement is both acid and base catalyzed, and proceeds best at a suitable rate at a pH outside the range of about 6.6 to about 9.4.

It has been observed experimentally that when an enzyme with 14 or less sulfhydryl donating residues is polymerized onto a support, the results are unreliable.

An example of an enzyme useful in the use of the present method is glucose oxidase (G.O.) obtained from *Aspergillus niger*, M.W. 154,000. While there is currently some question as to the exact number of sulfhydryl donating residues in G.O.'s primary structure, the reported values are 4 and 7 [4 residues reported by Pazur, H. H., Kleepe, K., and Cepure, A.; Archives of Biochemistry and Biophysics, V. 3, p. 351 (1965); and 7 residues were reported by Nakamura, S., and Fujiki, S.; Journal of Biochemistry, Tokyo, V. 63, p. 51 (1968)]. Because G.O. shows a low content of cysteine and cystine, this makes it useful in the present method due to its very extensive use in clinical biochemistry.

An example of a protein rich in cysteine and cystine sulfhydryl donating groups is bovine serum albumin (BSA), M.W. 66,000. BSA has been reported to contain 36 sulfhydryl donating groups. As used herein "sulfhydryl donating" group or residue is used to include cystine, which contains one —S—S— linkage which may be interchanged to yield —SH HS—, and cystine, which contains one —SH group. The composition of the amino acid residues of some proteins is available in "A Compilation of Amino Acid Analyses of Proteins VIII", Analytical Biochemistry, 66, 303/329 (1975), by Donald M. Kirshenbaum and other various articles in the series by Kirshenbaum.

An example of a useful inorganic support for the present invention is porous particulate alumina, its use and desired properties will be discussed later.

The method of the present invention is useful to form a composite using at least two enzymes, two non-enzymatic proteins, or one enzymatic protein and one non-enzymatic protein, the primary determinant of the method being the relative cysteine and cystine contents of the two participating proteins. Although, in the discussion of the method in general, for simplicity only two participating proteins are discussed, the method is equally useful in the case of the immobilization of multiple proteins or enzymes which are sulfhydryl poor, with one or more sulfhydryl rich proteins. For example, L-amino acid oxidase (M.W. 135,000) with about 14 sulfhydryl residues may be immobilized with G.O., maximum 7 sulfhydryl residues. This may be accomplished simultaneously with a single sulfhydryl rich protein, such as BSA. The resultant composite would be one of the enzyme-enzyme-protein-support type.

With respect to the preferred support to be used in the method of the present invention, the particulate alumina is washed with distilled water after having been sieved with an appropriate size sieve. The particles are usually on the order of 0.1 to 0.2 microns average diameter, with a high cavity content to increase the loading mass of enzyme per unit mass of support.

The support is then preferably air dried, with a final distilled water wash and then placed under 6 M HCl for about two hours. This procedure is believed to activate the alumina to facilitate deposition of the proteins. The activated alumina is again washed and dried. The resultant alumina can be stored under distilled water, a suitable buffer, or used at once.

The sulfhydryl rich protein, for example BSA, is dissolved in water and mixed with beta-mercaptoethanol, allowed to react, and then centrifuged. The supernatant is applied to a gel-permeation chromatography column, and the purified protein fractions are isolated. Phosphate buffer has been shown to be an acceptable reagent for BSA elution from the gel column. Also, a trace of NaCN or toluene is usually incorporated into the buffer to control bacterial activity on the column.

To prepare the desired enzyme for immobilization, different procedures are necessary for each enzyme.

This is due to the fact that each enzyme is sensitive to different ions, pH, temperature, and other solution factors. In the method, G.O. has been a particularly suitable protein. In the use of G.O., typically, a few grams of the crude protein are dissolved in distilled water with a phosphate buffer at about pH 6.0. The solution is mixed with enzyme grade ammonium sulfate and centrifuged. The resultant precipitate is discarded, and the supernatant liquid filtered. A second portion of ammonium sulfate is added, and the mixture is stirred. The mixture is centrifuged, and the precipitate isolated and dissolved in buffer. The G.O. is then isolated by gel permeation chromatography.

To form the composite, one of the proteins is mixed with the support and allowed to deposit on the support. The second (or as the case may be additional proteins) protein is added and allowed to deposit on the support. After sufficient time has elapsed for each protein to be deposited, the composite solution is adjusted to a suitable pH which facilitates sulfhydryl rearrangement.

In accomplishing the deposition on the support, the enzyme or other protein is preferably first deposited (e.g., sorbed or impregnated) in or on the support. "Sorbed" is defined to include adsorption or absorption by soaking the support with an aqueous solution of the enzyme. The aqueous solution is preferable buffered to a pH of about 7.5 to 9 to prevent premature polymerization thereof. However, if there are multiple proteins to be sorbed onto the support, the pH's of each deposition step may be slightly above or below the suggested pH range depending upon the pH requirements of each protein. The amount of enzyme used per given weight or volume of support can vary widely because of wide differences in porosity and surface activities of the supports as well as the variation in purity and composition of enzyme preparations which can be used in practicing this invention. The immobilized enzyme composite should contain at least about $1 \times 10^{-4}$ Enzyme Units (U.) per cubic centimeter for practical efficiency. The enzyme concentration in the reaction solution can be in the range of about 0.01% to about 90% by weight, depending on solubility parameters.

An Enzyme Unit (U.) of biological activity has been defined as the amount of active enzyme which converts substrate to product at the rate of one micromole per minute.

The enzyme composite in solution is adjusted to the pH which facilitates polymerization with respect to the last protein deposited. The pH is adjusted immediately after initial contact with the support or shortly after all contact has taken place, as long as premature polymerization does not prevent sorption on or in the support. This pH adjustment is accomplished by the addition of ordinary acids (e.g. HCl or $H_2SO_4$), bases (e.g. NaOH or KOH), or buffers (e.g. acetate or phosphate buffers) as required. Preferably, dilute buffer solutions which do not detrimentally affect the enzyme are employed, although strong acids and bases can be used under conditions which do not materially denature the enzyme. A preliminary testing can establish whether or not a particular pH adjusting additive will detrimentally affect the enzyme.

It is an important feature of the present invention that the cysteine and cystine poor enzyme or protein, and the cysteine and cystine rich protein or enzyme be deposited on the support prior to adjusting the pH to facilitate polymerization or shortly (e.g. a few minutes) thereafter. Being in the form or state of an enzyme or protein "monomer", it can most efficiently penetrate and permeate the support to obtain the maximum amount of enzyme per unit of surface area as compared to larger units which are a few "monomer" units long. In certain cases where necessary, the enzyme can be first reacted with a mercaptan such as beta-mercaptoethanol or cysteine to "depolymerize" any enzyme before contact with the support and to facilitate polymerization on the support. The composition of the support is not particularly critical as long as it is inert, dimensionally stable, and provides sufficient surface area for retention of enzyme and protein. The support can be porous, fluid-permeable membranes, as disclosed in U.S. Pat. No. 3,839,175, or porous particulates, as disclosed in U.S. Pat. No. 3,850,751. When porous supports are used, they should be sufficiently porous and sorptive enough to retain enough enzyme and protein to form a biologically active composite. In the preferred embodiments of the present invention, the immobilized enzyme-support composite will exhibit at least about $1 \times 10^{-4}$ Enzyme Units (U.) of activity per cubic centimeter of composite. Low enzyme activities in the composite are often due to impure enzyme sources used in the preparation.

It was found that the porous particles or the porous matrix having a volume porosity in the range of 10 percent to 80 percent, and preferably in the range of 15-50 percent are very suitable for use in the present purposes. The pore size of the support is critical in that it should have pores large enough to allow diffusion of the enzyme into the pores to be deposited in the inner surfaces of the particles of the composite. As noted above, G.O. is a relatively large protein when compared to its cysteine and cystine rich counterpart, BSA. Average pore size diameters of the porous particulates in the range of 0.01 micron to 10 microns are suitable for most applications with 0.01 to 2 being preferred for efficiency and economy.

The porous particulate support can be refractory ceramic oxide powders such as alumina powder, zirconia powder, magnesia powder, silica powder, thoria powder, glass powder, powdered clay, powdered talc, and the like. The particle size of the porous particulates is not critical, although a size range of −5 mesh to +400 mesh is practical. For efficiency and economy, the size fraction of −20 to +100 mesh (U.S. Sieve) can be used.

Porous, inert, rigid, dimensionally stable, refractory oxide, fluid permeable, membrane supports can be prepared by compacting refractory oxide powders to form a "green compact" of the desired configuration such as bars, sheets, etc. The green compacts are then fired for a period of time, and at a suitable temperature sufficient for sintering to yield porous, desired refractory supports. The sintering should not be conducted at temperatures or for periods of time which would cause a collapsing or coalescence of the particles to form a nonporous body. A convenient indication of the degree of sintering is a comparison of the actual density of the fired compact as compared to the theoretical density of the oxide being fired. Of the many oxides which can be used for the present purposes, alumina is preferred for its chemical durability and ease of fabrication.

In forming the support from a powdered refractory oxide, a powdered particle size is selected to yield a sintered compact having a porosity and pore size in the range set forth above. The techniques for compacting and sintering of the porous supports are well-known in the art. Generally, the compacting pressures are in the range of 1,000 psi to 10,000 psi and sintering temperatures are in the range of 1,000° to 1,700° C. are commercially expedient. Additional details on compacting and sintering of refractory oxides are set forth in the book "Oxide Ceramics", by E, Ryshewitch, published in 1960 by Academic Press, New York, N.Y.

The porous matrix can be in any geometric shape such as rods, cylinders, discs, plates, bars, blocks, and the like.

Other suitable supports can be in the form of natural and synthetic fibers such as polypropylene, polyethylene, cotton, wool, nylon, rayon, polyester or acrylic fiber. The support can also be a blend of both natural and synthetic fibers or can be inorganic fibers made from carbon, asbestos, glass, or similar fibrous ceramics, such as aluminum silicates. Fibrous forms of metals such as copper and stainless steel can also be used. Support fiber diameters can range from about 0.001 to about 0.25 inch. Such fibrous materials are quite useful in forming filter cartridges as in U.S. Pat. No. 3,828,934, for in-line filtration applications where filtration and treatment with immobilized enzymes are accomplished in one application.

For convenience in disclosure, all patent documents and publications mentioned herein are incorporated by reference. In the examples that follow, all parts are parts by weight, all percentages are weight percentages, and all temperatures are in °C., unless stated otherwise.

EXAMPLE 1

Forty grams of particulate porous alumina were washed with two liters of distilled water by swirling in a flask and decanting the cloudy supernatant liquid. The particulate alumina had a particle size in the range of from $-60$ to $+70$ mesh (U.S. Sieve) and an average pore size diameter of about 0.1 to 0.2 microns. Before washing, the alumina was resieved with an 80 mesh sieve. The alumina was allowed to stand under 200 ml of 6 N HCl for one hour. The acid was then discarded, and the alumina was washed with distilled water until clear, and then placed under suction with 200 ml more of distilled water. The resultant alumina could be stored under distilled water, Tham, [Tris (hydroxymethyl) aminomethane] buffer (pH 8.8) or used at once.

EXAMPLE 2

Five grams of Bovine Serum Albumin (BSA) were dissolved in 50 ml of distilled water to which was added 0.15 ml of a 0.2 M betamercaptoethanol solution. The resultant solution was stirred for one hour. The BSA solution was then centrifuged at 10,400 gravity forces for 30 minutes. An aliquot of the BSA solution was applied to a Sephadex G-50 column and eluted with $5\times 10^{-3}$ M NaCN. The selected eluted fraction of purified BSA was collected, and could be used at once or stored at $-70°$ F. until needed.

EXAMPLE 3

Fifteen grams of Sigma Type II Glucose Oxidase (G.O.) was dissolved in 150 ml of a buffer containing $5\times 10^{-3}$ M phosphate, at pH 6.0, which contained $1.5\times 10^{-4}$ M NaCN. To this solution was added 60 grams of enzyme grade $(NH_4)_2SO_4$ slowly. The resulting cloudy mixture was centrifuged at 14,600 gravity forces for one-half hour. The precipitate was discarded, and the supernatant liquid was filtered through a Whatman #1 filter. A second 60 gram portion of enzyme grade $(NH_4)_2SO_4$ was added to the solution, and the mixture was centrifuged at 14,600 gravity forces. The resultant precipitate was dissolved in 20 ml of the above buffer. This solution was applied to a Sephadex G-25 column (for example $8\times 80$ cm) and eluted with the above buffer. One hundred ml of the major peak from the G-25 column were separated. This 100 ml fraction was mixed with the cleaned, treated alumina of Example 1. This mixture was shaken for one-half hour at 0°–5° C. and then 10 ml of the Bovine Serum Albumin (BSA) of Example 2 was added. After adding the BSA, the pH of the mixture was adjusted to pH 5.0 with 0.1 M HCl. The resultant enzyme-protein-alumina composite was shaken gently for two hours at 0° and 5° C. Finally, the composite was washed with 2 liters of 0.2 M $(NH_4)_2SO_4$, then by 4 liters of distilled water.

The composite was stored under distilled water. The activity of the composite was measured using a Yellow Springs Instrument Company oxygen electrode, model 53, and determined to be 12 U/ml of composite.

What is claimed is:

1. A process for the immobilization of proteins having a relatively low cystine and cysteine content on a support to form a biologically active protein-support composite, in the absence of a cross-linking agent, consisting essentially of the steps of:
   selecting a first protein having a sum total of two times the number of the cystine amino acid residues plus al the cysteine amino acid residues equaling at least about 14 per mole of said protein;
   selecting at least a second protein, which comprises an enzyme, having a sum total of two times the number of the cystine amino acid residues plus all of the cysteine amino acid residues equaling less than 14 per mole of said protein;
   depositing said selected proteins on an inert support; and
   copolymerizing said first and second proteins on said inert support in the absence of a cross-linking agent to provide a protein-support composite containing an amount of enzyme comprising said protein to result in the composite having at least $1\times 10^{-4}$ enzyme units of activity per cubic centimeter of said composite.

2. The process of claim 1, wherein said enzyme is glucose oxidase.

3. The process of claim 1, wherein said enzyme is L-amino oxidase.

4. The process of claim 1, wherein said copolymerization is accomplished at a pH in the range of about 5 to 10.

5. The process of claim 4, wherein said pH is in the range of about 7.5 to about 9.

6. The process of claim 1, wherein said inert support is a refractory oxide powder.

7. The process of claim 1, wherein said support is a porous matrix prepared by compacting and sintering a refractory oxide powder.

8. The process of claim 1, wherein said inert support is alumina.

9. The process of claim 1, wherein said copolymerization is accomplished at a temperature in the range of 0 degrees centigrade to 30 degrees centigrade.

10. The process of claim 9, wherein said temperature is in the range of 15 to 25 degrees centigrade.

11. The process of claim 1, wherein said copolymerization is accomplished over a period of time of at least two hours.

12. The biologically active protein-support composite product of the process of claim 1.

13. The product of claim 12, wherein said enzyme is glucose oxidase.

14. The product of claim 12, wherein said enzyme is L-amino acid oxidase.

15. The product of claim 12, wherein said inert support is a refractory oxide powder.

16. The product of claim 12, wherein said inert support is alumina.

17. The product of claim 12, wherein said inert support is a porous matrix prepared by compacting and sintering a refractory oxide powder.

* * * * *